United States Patent [19]

Brazier

[11] Patent Number: 4,995,868
[45] Date of Patent: Feb. 26, 1991

[54] CATHETER

[75] Inventor: Gary B. Brazier, Great Oakley, United Kingdom

[73] Assignee: Bard Limited, Crawley, United Kingdom

[21] Appl. No.: 412,993

[22] Filed: Sep. 26, 1989

[30] Foreign Application Priority Data

Oct. 12, 1988 [GB] United Kingdom ............... 8823905
Nov. 28, 1988 [GB] United Kingdom ............... 8827751

[51] Int. Cl.⁵ ............................................ A61M 29/00
[52] U.S. Cl. ................................... 604/105; 604/104
[58] Field of Search ........................... 27/24.1, 24.2; 604/104–109; 606/191, 198

[56] References Cited

U.S. PATENT DOCUMENTS

| | | | |
|---|---|---|---|
| 1,828,986 | 10/1931 | Stevens | 604/105 |
| 3,108,595 | 10/1963 | Overment | 604/105 |
| 3,241,554 | 3/1966 | Coanda | 604/105 |
| 3,261,357 | 7/1966 | Roberts et al. | 604/105 |
| 3,490,457 | 1/1970 | Peterson | 604/105 |
| 3,713,447 | 1/1973 | Adair | 604/105 |
| 3,799,172 | 3/1974 | Szpur | 604/105 |
| 3,946,741 | 3/1976 | Adair | 604/105 |
| 4,228,802 | 10/1980 | Trott | 604/105 |
| 4,921,484 | 5/1990 | Hillstead | 604/104 |

FOREIGN PATENT DOCUMENTS

| | | |
|---|---|---|
| 688450 | 3/1953 | United Kingdom . |
| 690391 | 4/1953 | United Kingdom . |
| 955490 | 4/1964 | United Kingdom . |
| 1014570 | 12/1965 | United Kingdom . |
| 1046478 | 10/1966 | United Kingdom . |
| 1463269 | 2/1977 | United Kingdom . |

Primary Examiner—Stephen C. Pellegrino
Assistant Examiner—Ralph Lewis
Attorney, Agent, or Firm—Dennison, Meserole, Pollack & Scheiner

[57] ABSTRACT

A catheter, for example for bladder drainage, formed of two coaxial tubes and including near the distal end of the outer tube an expandable and contractable retention structure, for example Malecot wings, and at the proximal end of the inner tube a hollow connector for attachement to a fluid supply or drain, comprises actuating means to effect relative sliding movement of the proximal ends of the tubes so as to expand or contract the retention structure, and which means further include a housing secured to the proximal end of the outer tube and so dimensioned that when the retention structure is moved into the contracted position the hollow connector is withdrawn into the housing. This configuration of actuating means prevents both inadvertent connection of a fluid supply or drain when the retention structure is in the contracted position and attempted removal of the catheter when the retention structure is in the expanded position.

18 Claims, 2 Drawing Sheets

CATHETER

BACKGROUND OF THE INVENTION

The present invention relates to a catheter. The invention is particularly concerned with a catheter suitable for obtaining suprapubic access and drainage. The following description is mainly directed to this type of catheter, but it will be understood that the invention is also applicable to other types.

A suprapubic catheter is conventionally inserted through the abdominal wall into the bladder by means of trocar projecting through the catheter tip. The trocar is withdrawn when the catheter tip is in place. A variety of means have been proposed to ensure that once in place the catheter tip is retained in the bladder. For example, a Foley bladder catheter includes an inflatable balloon at its distal end (i.e. within the bladder), an inflation channel in the walls of the catheter, external means of supplying inflation fluid through the channel and valve means to keep the fluid in place and the balloon inflated.

An alternative retention means uses a resiliently protruding formation which can be elastically deformed by an actuator to the protruding position for retention and to a non-protruding disposition for catheter insertion and removal. Examples are (i) "wings" formed from the catheter wall [Malecot catheters]or (ii) an increased diameter portion of the catheter tube at its tip [De Pezzer].

The tip formation can for example be held in a protruding disposition by tension in an actuating rod or line which extends to the proximal end of the catheter (see British Patent Specification Nos. 688,450, 955,490, 1,014,570, 1,046,478 and 1,463,269 and U.S. Pat. Nos. 1,828,986, 3,241,554, 3,261,357, 3,713,447 and 4,228,802). U.S. Pat. No. 3,490,457 to Petersen discloses a catheter in which wings are brought into a projecting disposition by pulling on a tip insert with a thread which extends the length of the catheter tube to its proximal end. When the wings are erect, the thread is removed.

For many purposes, the most convenient combination of catheter tubing and actuating means for effecting the expansion and contraction of a distal protruding portion is provided by employing two concentric tubes secured together at their distal ends, the inner tube providing a fluid flow passage and the outer tube incorporating near its distal end an expandable portion which can be brought into its protruding position by relative axial movement of the two tubes. An early example of such concentric tube catheters is described in U.S. Pat. No. 3,108,595 to Overment. A later example, U.S. Pat. No. 3,946,741 to Adair, relates to the provision of sealing means to prevent leakage through the outer tube.

Problems arise in using catheters with such expandable tip portions in ensuring or checking whether the tip is in the expanded or contracted position inside the body. Although in principle it is possible to check by inspecting the external portions of the catheter, this is only satisfactory if the person making the inspection is sufficiently familiar with the particular catheter to know what internal position is indicated by the relative external position. Thus in practice there arises the likelihood that the catheter tip will be left in the body with its intended protruding portion in the contracted state, and thus vulnerable to being inadvertently removed from the body, or that attempts will be made to remove the catheter from the body while the tip is in the protruded state, with consequent discomfort to the patient and damage to the body tissue.

SUMMARY OF THE INVENTION

The invention relates to a catheter having an improved actuating means to ensure that the tip is in the required expanded state for retention in the body or contracted state for insertion and removal from the body.

According to the invention there is provided a catheter comprising an inner tube having a distal end for insertion into a human or animal body and a proximal end to be located outside the body, a hollow connector secured to the proximal end of the inner tube for attachment to a fluid supply or fluid drain, an outer tube concentric with the inner tube and having a distal end secured to the distal end of the inner tube, a proximal end to be located outside the body and an expandable and contractable retention structure adjacent to the distal end, actuating means for the expandable retention structure including an attachment to the inner tube at or near its proximal end and an attachment to the outer tube at or near its proximal end, in which the said attachments include elements to effect relative sliding movement of the proximal end of the tubes and thereby to expand or contract the retention structure, wherein a housing is secured to the proximal end of the outer tube and is so dimensioned that when the retention structure is in a contracted condition, the inner tube connector is located within the housing and when the retention structure is in an expanded condition, the inner tube connector protrudes beyond the housing.

The catheter according to the invention offers the advantage that the fluid supply or drain can only be securely attached to the inner tube connector when the retention structure is in the expanded state and thus firmly held within the body. When the catheter is to be removed from the body, the fluid supply or drain is detached from the inner tube connector, the actuating means is operated to move the inner tube connector into the housing and the retention structure into its contracted state so as to facilitate withdrawal of the catheter from the body. The invention accordingly provides a visual means of checking that the retention structure is in the required condition, and avoids inadvertent connection of a fluid supply or drain when the retention structure is in the contracted state.

The preferred type of retention structure for catheters according to the invention is a Malecot structure. This comprises several, usually four, axial slits in the outer tube near its distal end. To form the expanded state, relative movement of the inner and outer tubes raises portions of the tube between the slits to form "wings". To form the contracted state, relative movement of the tubes returns the portions to the tubular shape.

The preferred elements to effect relative sliding movement of the tubes are protruding pins attached to the inner tube and a sleeve attached to the outer tube and having axial grooves or slots to receive the pins. At each end of the grooves or slots there is preferably provided a detent. Snapping the pins into position in the detent not only holds the elements, and thus the retention structure, in the desired position, but also indicates to the user that the desired position has been reached.

The housing to receive the inner tube connector preferably forms a part of the sleeve and can if desired be formed as an integral part thereof.

The internal shape of the housing preferably conforms closely to the external shape of the connector. In most instances the connector has a substantially circular cross section and the internal shape of the housing should then also be substantially circular, with an internal diameter slightly larger than the external diameter of the connector. The external shape of the housing can be chosen to suit the particular connections required and may usefully include roughening, ribs or grooves, to assist handling of the housing by the user.

In a particular preferred embodiment of the invention, the housing is formed at least in part by an internally threaded nut rotatably connected to the outer tube attachment. The internal threading of the nut is chosen to engage the pins attached to the inner tube. The number of threads is dictated by the number of pins: a two pin structure requires a twin start thread; a three pin structure a three-start thread, etc. The nut preferably has a generally cylindrical outer shape and the outer tube attachment is preferably provided with a portion of similar external shape and diameter to the nut. Such similar cylindrical shapes facilitate expansion or contraction of the retention structure in that the user can conveniently hold the outer tube attachment with one hand while turning the nut with the other hand. This convenience in manipulation can be further enhanced by providing both the outer tube attachment and the nut with external roughening, ribs or grooves.

The angle of the threads is preferably such as to effect the full sliding movement by a rotation of the nut of less than 180°, thereby making it easy for the user to raise or lower the retention structure without removing the hands from the nut or attachment.

In this preferred embodiment, the nut can conveniently provide at least part of the housing for the inner tube connector.

The catheter preferably includes at least one seal between the inner and outer tubes so as to prevent fluid leakage through the space between them. The seal or seals can be part of the actuating means, but can alternatively or additionally be included in the expandable retention structure, for example by an annular member located on the inner tube at Point such that the outer tube abuts against the annular member when the retention structure is in the expanded state.

A convenient version of attachment is a luer connection. In its preferred form this comprises, as the hollow connector forming part of the catheter, and attached to the proximal end of the inner tube, a female spigot with a tapered internal channel and external shaped lugs. As part of a fluid tube or syringe to which the catheter is to be connected the connection includes a hollow male insert with a rotatable external fitment having threads to engage the shaped lugs. For the purposes of the present invention the angle of the threads should be complementary with the threading of any nut employed to move the pins attached to the inner tube. This complementary threading ensures that rotating the luer connection to effect attachment of the two parts does not simultaneously tend to rotate the nut in a direction which would return the extended structure to the contracted state.

The pins are preferably formed as an integral component with the female part of the luer connection. In this description the component so formed is designated as a luer slider.

The various parts of the catheter are preferably formed in a medically approved plastic, for example polyurethane or pvc. The materials for the inner and outer tubes should be chosen to ensure that these do not tend to stick to each other. This can be achieved by selecting different plastic materials, for example different grades of pvc, for the two tubes. Alternatively or additionally a lubricant material, for example polytetrafluorethylene, can be incorporated on the surface of one or both tubes so as to assist their relative sliding action. The incorporation of the lubricant material can for example be effected by coextrusion of the lubricant material when forming the tube.

The invention thus provides an easy to use retainable catheter which gives the nurse an immediate indication of its retention element inside the body, which can only be connected to associated tubes or other items if it is in the position for retention and which is clearly restored to the non-retention position before being removed from the body.

BRIEF DESCRIPTION OF THE DRAWINGS

One version of the catheter according to the invention is described below with reference to the accompanying drawings, in which.

DESCRIPTION OF PREFERRED EMBODIMENT

Figure 1:
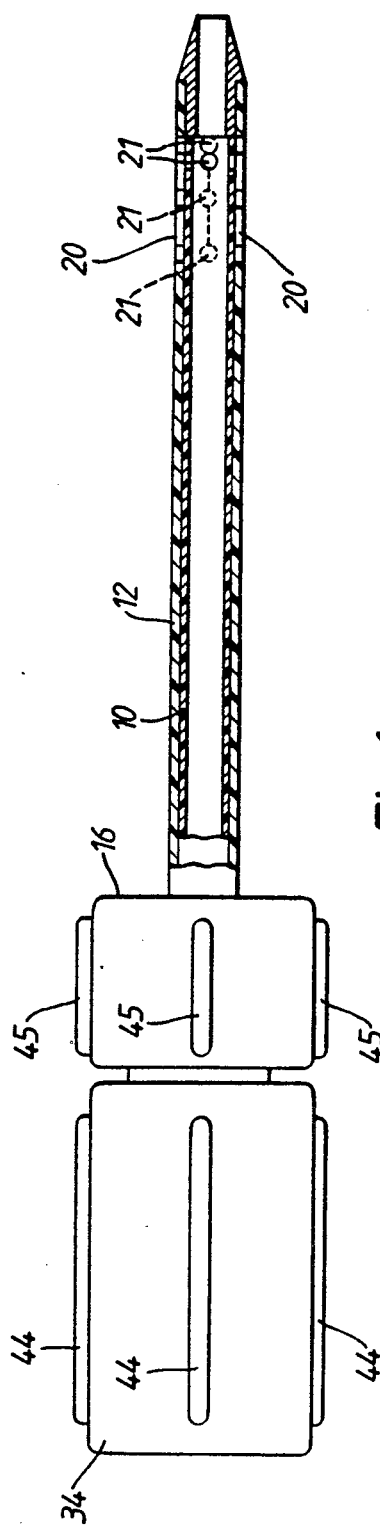
FIG. 1 is a view, partly in section, of a catheter in which the retaining wing structure is in the contracted position.
Figure 2:
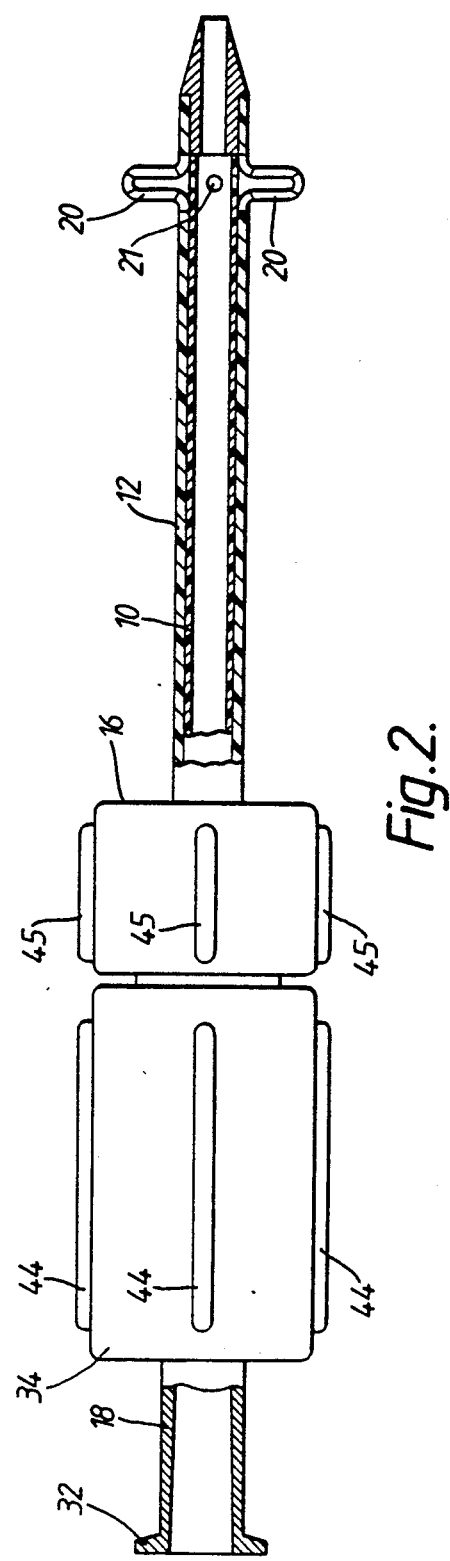
FIG. 2 is a view of the catheter as shown in FIG. 1, but with the retaining wing structure in the expanded position.
Figure 3:
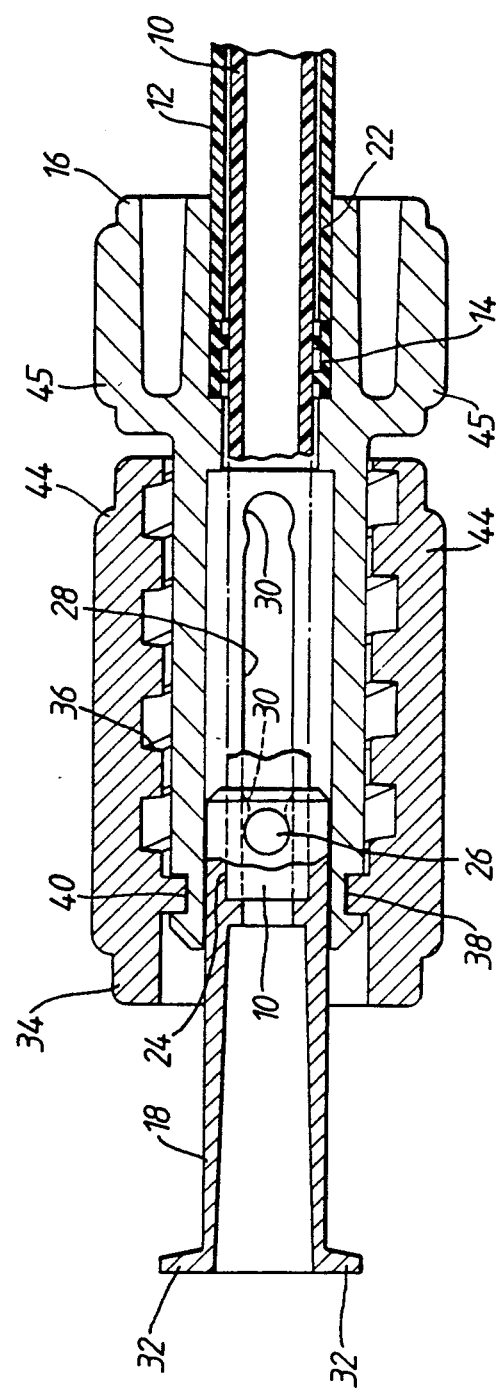
FIG. 3 is a sectional view of the proximal end of the catheter shown in FIGS. 1 and 2, but on a larger scale.

The catheter comprises an inner tube 10 and an outer tube 12, an annular seal 14, an attachment 16 for the outer tube 12 and a luer slider 18 as an attachment for the inner tube 10. The inner and outer tubes 10 and 12 are formed of different grades of polyurethane.

At the distal end (right hand side as viewed in the figures), the two tubes 10 and 12 are sealed together in a tapered configuration. Adjacent to the taper the outer tube 12 is slit to form a Malecot retaining device i.e. four longitudinal strands 20 which expand outwards to form protruding wings if the inner tube 10 is moved to the left (as viewed).

The inner and outer tubes 10 and 12 include circular ports 21 along the length of the strands 20. For the inner tube 10 the ports 21 give additional openings for passage of fluid into or out of the catheter. For the outer tube 12 the ports 21 facilitate the expansive movement of the strands into the wing-like protrusion.

At its proximal end 22 the outer tube 12 is solvent bonded to the attachment 16. The inner tube is solvent bonded at 24 into the luer slider 18. Projecting pins 26 on the luer slider 18 engage in elongated slots 28 within the attachment 16. At each end of each slot 28 is a shaped detent 30 (only one such detent being illustrated) to hold the engaging pin 26 in the respective end position. The luer slider 18 has projecting lugs 32 to lock into corresponding grooves on the tubing or other fitment (not shown) to which the catheter is to be attached.

A cylindrical nut 34 is rotatably disposed about the left hand end of the attachment 16 and has internal threads 36 engaging the pins 26 on the luer lock 18. The nut 34 is prevented from moving sideways relative to the attachment 16 by means of a cooperating annulus 38 on the nut 34 and circular groove 40 on the attachment 16.

The nut 34 has external ribs 44 to assist the user in rotating it. Together the attachment 16 and nut 34 provide a casing to receive the luer slider 18 when this is moved to the left hand end of slot 28 i.e. when the strands 20 are in the non-expanded state.

The right hand end of the attachment 16 is shaped to an external diameter the same as the nut 34 and also has external ribs 45. The internal diameter of the right hand end of the attachment 16 is chosen so as to receive the outer tube 12 and the seal 14 disposed about the inner tube 10.

The catheter is inserted into the bladder with the assistance of a trocar (not shown). After the trocar is withdrawn, the Malecot strands 20 are expanded by holding the ribs 45 stationary while rotating the nut 34. This moves the luer slider 18 out of the housing formed by the attachment 16 and nut 34 and allows a fluid drain tube to be connected to the attachment 16.

Arrival of the luer slider 18 at its required position is confirmed to the user by a slight snap action detected through the nut 34 as the pins 26 enter the detent 30.

When the catheter is to be withdrawn, the drain tube is removed from the luer slider 18 and the nut 34 is rotated in the opposite direction, thereby returning the slider 18 into the housing and restoring the strands 20 to a contracted state for removal from the bladder. Arrival of the luer slider 18 at the other end of its travel is again confirmed to the user by a snap action as the pins 26 enter another detent 30.

I claim:

1. A catheter comprising an inner tube having a distal end for insertion into a human or animal body, said inner tube having an opening defined therein at or near the distal end thereof to establish a fluid path, and a proximal end to be located outside the body, a hollow connector secured to the proximal end of the inner tube for attachment to a fluid supply or fluid drain; an outer tube concentric with the inner tube and having a distal end secured to the distal end of the inner tube, a proximal end to be located outside the body and an expandable and contractible retention structure adjacent to the distal end; actuating means on the proximal ends of said inner and outer tubes for the expandable retention structure including means for enabling and effecting relative sliding movement of the proximal ends of the tubes and thereby to expand or contract the retention structure and respectively define an expanded condition or a contracted condition, wherein a housing is secured to the proximal end of the outer tube and is so dimensioned that when the retention structure is in a contracted condition, the inner tube connector is located within the housing and when the retention structure is in an expanded condition, the inner tube connector protrudes beyond the housing.

2. A catheter as claimed in claim 1, wherein the hollow connector is one part of a luer connection, connectable to, as the other part of the luer connection, a complementary fitting on an external fitment such as a fluid tube or syringe.

3. A catheter as claimed in claim 2, wherein the means for effecting relative sliding movement of the proximal ends of the tubes are protruding pins, which are attached to the inner tube, and a sleeve, which is attached to the outer tube and has axial grooves or slots to receive the pins.

4. A catheter as claimed in claim 3, wherein a detent is provided at each end of the axial grooves or slots.

5. A catheter as claimed in claim 3, wherein the housing to receive the inner tube hollow connector is defined at least in part by the sleeve.

6. A catheter as claimed in claim 5, wherein the internal shape of the housing and the external shape of the hollow connector are of substantially circular cross section, the internal diameter of the housing being slightly larger than the external diameter of the hollow connector.

7. A catheter as claimed in any claim 6, wherein the housing is formed at least in part by an internally threaded nut rotatably connected to the outer tube attachment sleeve.

8. A catheter as claimed in claim 7, wherein the internally threaded nut has a generally cylindrical outer shape, said sleeve having a distal end portion beyond said nut of generally cylindrical shape similar to said nut.

9. A catheter as claimed in claim 8, wherein the angle of the threads is such as to effect the full sliding movement by a rotation of the nut of less than 180°.

10. A catheter as claimed in claim 1, wherein the means for effecting relative sliding movement of the proximal ends of the tubes are protruding pins, which are attached tot he inner tube, and a sleeve, which is attached to the outer tube and has axial grooves or slots to receive the pins.

11. A catheter as claimed in claim 10, wherein a detent is provided at each end of the axial grooves or slots.

12. A catheter as claimed in claim 11, wherein the housing to receive the inner tube hollow connector is defined at least in part by the sleeve.

13. A catheter as claimed in claim 12, wherein the internal shape of the housing and the external shape of the hollow connector are of substantially circular cross section, the internal diameter of the housing being slightly larger than the external diameter of the hollow connector.

14. A catheter as claimed in claim 1, wherein the internal shape of the housing and the external shape of the hollow connector are of substantially circular cross section, the internal diameter of the housing being slightly larger than the external diameter of the hollow connector.

15. A catheter as claimed in claim 14, wherein the housing is formed at least in part by an internally threaded nut rotatably connected to the outer tube.

16. A catheter as claimed in claim 15, wherein the internally threaded nut has generally cylindrical outer shape.

17. A catheter as claimed in claim 16, wherein the angle of the threads is such as to effect the full sliding movement by a rotation of the nut of less than 180°.

18. A catheter as claimed in claim 15, wherein the angle of the threads is such as to effect the full sliding movmeent by a rotation of the nut of less than 180°.

* * * * *